United States Patent [19]

Karlsson

[11] Patent Number: 5,735,832
[45] Date of Patent: Apr. 7, 1998

[54] REINFORCED MICRODIALYSIS PROBE

[75] Inventor: Hans Karlsson, Sollentuna, Sweden

[73] Assignee: CMA/Microdialysis Holding AB, Solna, Sweden

[21] Appl. No.: 682,746

[22] PCT Filed: Feb. 1, 1995

[86] PCT No.: PCT/SE95/00095

§ 371 Date: Jul. 31, 1996

§ 102(e) Date: Jul. 31, 1996

[87] PCT Pub. No.: WO95/20983

PCT Pub. Date: Aug. 10, 1995

[30] Foreign Application Priority Data

Feb. 4, 1994 [SE] Sweden ............................ 9400377

[51] Int. Cl.⁶ .................................................. A61M 25/00
[52] U.S. Cl. ...................... 604/282; 604/27; 600/309
[58] Field of Search ............................ 604/19, 27, 29, 604/48, 95, 96, 36, 93, 280, 282, 264; 128/632

[56] References Cited

U.S. PATENT DOCUMENTS

| | | | |
|---|---|---|---|
| 4,694,832 | 9/1987 | Ungerstedt | 128/632 |
| 4,765,339 | 8/1988 | Jones | 128/632 |
| 5,106,365 | 4/1992 | Hernandez | 604/27 |
| 5,156,844 | 10/1992 | Aebischer et al. | 424/424 |
| 5,191,900 | 3/1993 | Mishra | 128/769 |
| 5,441,481 | 8/1995 | Mishra et al. | 604/29 |
| 5,607,390 | 3/1997 | Patsalos et al. | 604/29 |

FOREIGN PATENT DOCUMENTS

| | | |
|---|---|---|
| 0 401 179 | 12/1990 | European Pat. Off. . |
| 0 403 394 | 12/1990 | European Pat. Off. . |
| 3 342 170 | 1/1992 | Germany . |

*Primary Examiner*—Michael Powell Buiz
*Assistant Examiner*—Deborah Blyveis
*Attorney, Agent, or Firm*—Young & Thompson

[57] ABSTRACT

A microdialysis probe having a center tube surrounded by a thin dialysis tube (3), which is located between two tubular fitting parts (2, 5). With the purpose of reinforcing the probe and facilitating its withdrawal without any part of the probe remaining despite the fragility of the dialysis tube, the distal end of the center tube from within is fixedly joined to the distal fitting part (2), which also has a larger diameter than the dialysis tube (3).

7 Claims, 1 Drawing Sheet

REINFORCED MICRODIALYSIS PROBE

FIELD OF THE INVENTION

The invention relates to a microdialysis probe. A dialysis probe of this kind is described in SE-C-434 214.

BACKGROUND OF THE INVENTION

Microdialysis is a method of examination in which a probe is inserted into tissue in vivo, such that one side of a semi-permeable membrane is in contact with tissue and body fluid, while the other side is flushed or rinsed with a dialysis liquid which takes-up substances through the membrane, which substances can then be analyzed in the liquid that has flown past. This method has made large advances in recent years and the number of research publications relating to microdialysis have multiplied in frequency a thousand-fold in ten years.

The use in clinical and polyclinical activities for diagnostic purposes on human beings, however, has been held back, primarily because dialysis probes are relatively fragile by nature, which makes it difficult to insert and remove the probe. At least part of the probe must have a surface which consists of a thin, semi-permeable membrane which is easily broken, particularly when removing the probe. The problem is not as large during insertion, since during insertion an external tube is normally used which is removed after insertion while leaving the probe in place. This outer tube may have the form of a plastic tube which can be withdrawn and slit flush with the skin as the tube is gradually withdrawn, with the probe left in position.

However, when the probe is inserted into tissue of a living person, the probe must be able to retain its shape despite the stresses and strains that can be expected when the person moves. A still greater problem occurs when the probe is to be withdrawn after use. In the case of the known probe, withdrawal may result in part of it being left in the body.

SUMMARY OF THE INVENTION

Accordingly, it is an object of the invention to provide a microdialysis probe which is suitable for general human use when taking samples for a diagnostic purpose as a routine method. In particular the risk of material being left behind when the probe is withdrawn must be overcome.

These and other objects are achieved and the aforementioned risks avoided to the highest degree in accordance with the invention by modifying a microdialysis probe of the kind defined in the introduction in the manner defined in the characterizing clause of the following Claim 1. Preferred embodiments are defined in the depending Claims.

Because the distal end of the probe is fixedly joined to the center tube, safe withdrawal of this end is guaranteed. Furthermore, it is also ensured that no part of the mantle tube will remain, since even if the tube should be broken, the worst that can happen is only a certain degree of movement towards the distal end, which has a larger diameter and which when withdrawn from the insertion hole will entrain any pieces that may have broken off from the mantle tube.

BRIEF DESCRIPTION OF THE DRAWINGS

The invention will now be described in more detail with reference to an illustrative but not limiting embodiment thereof.

DESCRIPTION OF THE PREFERRED EMBODIMENT

Figure 1:
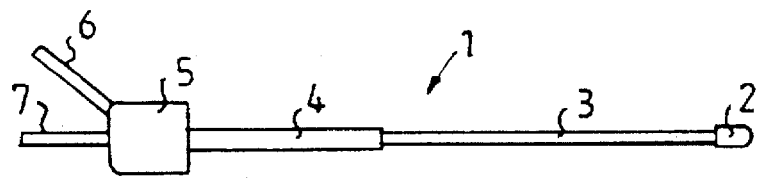
FIG. 1 is a schematic side view of a microdialysis probe.

The probe 1 shown in FIG. 1 has at its distal end an enlarged fitting in the form of a first tube 2 from which there protrudes a mantle tube 3, which is somewhat narrower. The mantle tube 3 extends to a second tube 4 and penetrates the second tube. In turn, the second tube 4 extends to a distal end-piece 5, from which two external connecting pipes 6 and 7 extend.

Figure 2:
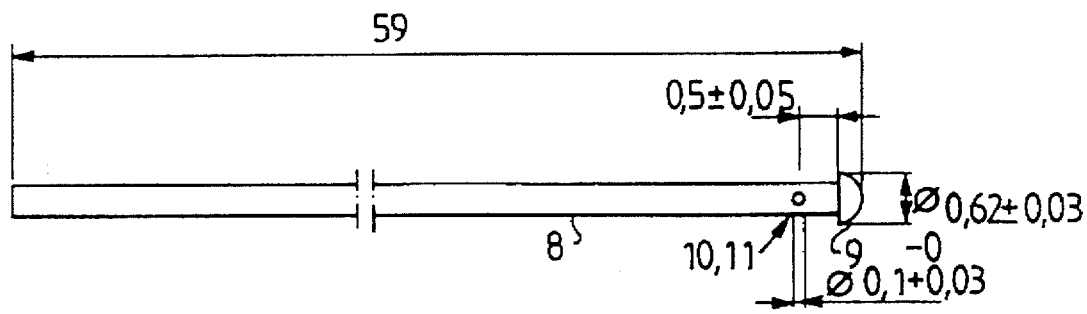
FIG. 2 illustrates a center tube.

In the invention, it is not actually the at least partially very thin mantle tube 3 which is the supporting structure. Rather the mantle tube encases a centre tube 8 which extends between the end-piece 5 and the fitting 2 and which is fastened to the fitting 2 so that the mantle tube 3 is essentially clamped between the fitting 2 and the distal end of the tube 4. The center tube is shown in FIG. 2, and is closed and enlarged at its distal end. As will be seen from FIG. 3, the center tube is taken up in the fitting 2, where it is accommodated, surrounded by a glue, preferably at least partially by shape conformity. If the tube 8 is made of plastic, the end of the tube is appropriately formed by melting.

Figure 4:
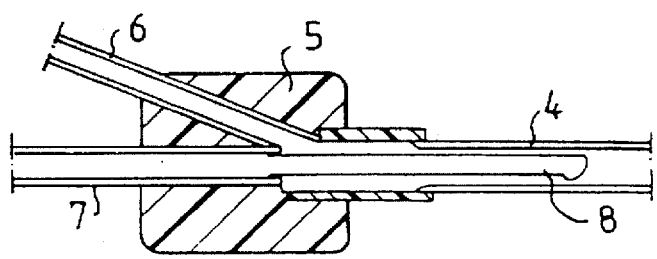
FIG. 4 shows a proximal end of a microdialysis probe also in larger scale and in section.

As will be seen from FIG. 4, the center tube 8 is connected in the end-piece 5 to one of the pipes 6 and 7, whereas the other of the pipes discharges into the space between the center tube 8 and the second tube 4. To facilitate symmetric and problem-free withdrawal, the center tube extends perfectly straight, from the end-piece 5 which is never inserted into the body, up to the thickening 9 at the distal end. Even should the membrane break in the actual passage through the skin—human skin can be relatively tough and elastic—the membrane will be withdrawn seated on the enlarged end at the distal end of the center tube.

EXAMPLE

Figure 3:
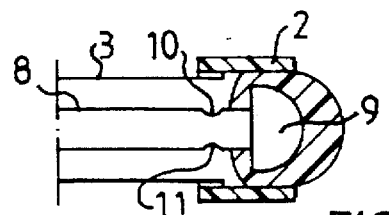
FIG. 3 illustrates in larger scale and in section a distal end of a microdialysis probe.

A tube of hard polyurethane having an outer diameter of 0.4 mm and an inner diameter of 0.12 mm was fused together at one end, so as to obtain an approximately hemispherical ball 9 having a diameter of 0.6 mm. Two opposing holes having a diameter of 0.1 mm were made at an axial distance of about 0.5 mm therefrom. This resulted in a center tube according to FIG. 2 having the measurements disclosed in the Figure. An outer part was manufactured by threading a membrane 3 of polyamide of the same type as that used in artificial kidneys and having a thickness of 50 μm and a diameter of 0.5 mm onto a mandrel. Hoses 2 and 4 having an internal diameter of 0.65 mm were applied from both sides and the ends of the hoses were glued firmly to the membrane with polyurethane glue. The whole was withdrawn from the mandrel and the center tube was fitted from the distal side, thus with the ball 9 last, whereafter glue was injected between the tube 2 and the ball 9, in accordance with what is shown in FIG. 3. A hose 7 was secured to the other end of the center tube, and another hose 6 was mounted with connection to the interspace between the tubes 4 and 8, the whole being surrounded by a moulded plastic 5.

In order to insert such a catheter some form of stiffening is required, for instance a surrounding cannula which can be removed after insertion. There are available steel cannula that are provided with two longitudinally extending weakenings which enable the cannula to be withdrawn and split into two halves so that it can be removed.

"Dialysis liquid" can now be pressed in through one of the connecting pipes 6, 7 in a known manner, and after taking up the substances through the semi-permeable mantle tube is collected from the other connecting pipe. It is preferred to use as the introduction pipe the pipe which is in direct communication with the space between the membrane tube and the center tube in view of the fact that the "dead space" is thereby minimized. The outcoming liquid volume is then subjected to conventional microanalysis, which forms no part of the present invention.

I claim:

1. A microdialysis probe, having a distal end comprising:

a center tube having a proximal end, a closed distal end, a side surface, and a distal aperture located in the side surface, said distal end of said center tube having an enlargement;

a semi-permeable mantle tube surrounding said center tube, said mantle tube having a proximal end and a distal end, said mantle tube being free of an external mounting for support thereof, said mantle tube and said center tube defining a space therebetween, said distal aperture opening into the space between the mantle tube and the center tube;

a fitting partially surrounding said mantle tube for supporting and partially exposing said mantle tube, said fitting including a first tube surrounding and fastened to said proximal end of said mantle tube, said fitting including a second tube surrounding and fastened to said distal end of said mantle tube, said second tube having a closed distal end, said enlargement of said center tube being fitted within said second tube.

2. A microdialysis probe according to claim 1, wherein the mantle tube has a wall thickness of 15–50 μm.

3. A microdialysis probe according to claim 2, wherein the mantle tube comprises one of polyamide and cellulose.

4. A microdialysis probe according to claim 1, wherein the first and second tubes are plastic.

5. A microdialysis probe according to claim 1, further comprising glue laid between the enlargement of the center tube and the distal end of the second tube, thereby attaching the center tube to said second tube and forming a closure at the distal end of the second tube.

6. A microdialysis probe according to claim 1, wherein the second tube forms an enlargement of the distal end of the probe, this enlargement having a larger outer diameter than the outer diameter of the mantle tube.

7. The microdialysis probe according to claim 1, further comprising a first external connecting pipe connected to the proximal end of said center tube, and a second external connecting pipe communicating with the space between said mantle tube and said center tube.

\* \* \* \* \*